(12) United States Patent
Colin et al.

(10) Patent No.: US 6,384,257 B1
(45) Date of Patent: May 7, 2002

(54) METHOD FOR PREPARING ALKYL HYDROGENO HALOSILANES (AHHS) BY CATALYTIC HYDROGENATION

(75) Inventors: Pascale Colin, Chassieu; Roland Jacquot, Francheville; Philippe Morel, Chuzelles, all of (FR)

(73) Assignee: Rhodia Chimie, Courbevoie Cedex (FR)

( * ) Notice: Subject to any disclaimer, the term of this patent is extended or adjusted under 35 U.S.C. 154(b) by 0 days.

(21) Appl. No.: 09/869,173

(22) PCT Filed: Dec. 21, 1999

(86) PCT No.: PCT/FR99/03214

§ 371 Date: Sep. 26, 2001

§ 102(e) Date: Sep. 26, 2001

(87) PCT Pub. No.: WO00/39132

PCT Pub. Date: Jul. 6, 2000

(30) Foreign Application Priority Data

Dec. 28, 1998 (FR) ............................................. 98 16693

(51) Int. Cl.$^7$ ................................................. C07F 7/08
(52) U.S. Cl. ....................................................... 556/474
(58) Field of Search ......................................... 556/474

(56) References Cited

U.S. PATENT DOCUMENTS 5,646,326 A * 7/1997 Schuler ...................... 556/474
5,856,548 A * 1/1999 Drose et al. ................ 556/474

FOREIGN PATENT DOCUMENTS

| EP | 0 714 900 A | 6/1996 |
| FR | 2 342 981 A | 9/1977 |

* cited by examiner

*Primary Examiner*—Paul F. Shaver
(74) *Attorney, Agent, or Firm*—Burns, Doane, Swecker & Mathis, L.L.P.

(57) ABSTRACT

The invention concerns the upgrading of a by-product of direct synthesis, namely $MeSiCl_3$, by vapor phase catalytic hydrogenation of said by-product to obtain $MeHSiCl_2$ with greater added value. The invention concerns a method for preparing $MeHSiCl_2$ by catalytic hydrogenation of $MeSiCl_3$ in the presence of a metal catalyst with high selectivity levels in $MeHSiCl_2$ economically and without having recourse to drastic and industrially unsuitable conditions. The invention uses a catalyst comprising a bimetal ruthenium/tin catalytic agent. Said catalytic agent is obtained by reacting ruthenium chloride and tin chloride in an acid medium. In practice, the catalyst is formed by a silica powder support impregnated by the ruthenium/tin catalytic agent.

34 Claims, No Drawings

METHOD FOR PREPARING ALKYL HYDROGENO HALOSILANES (AHHS) BY CATALYTIC HYDROGENATION

CROSS-REFERENCE

This application is a National Stage of International Application No. PCT/FR99/03214, filed Dec. 21, 1999, which International Application was published by the International Bureau in English on Jul. 6, 2000. This application claims priority to French Application 98/16693, filed Dec. 28, 1998.

The present invention relates to the catalytic hydrogenolysis of Si—X bonds (X=halogen, preferably Cl) present in compounds of the alkylhalosilane (ahs) type, for example methylchlorosilane, for the purpose of converting these ahs into alkylhydrohalosilanes (ahhs), for example methylhydrochlorosilane. In particular, the hydrogenolysis to which the invention relates is of the type that employs gaseous hydrogen and a metallic catalyst with production of hydrogen halide.

More particularly still, the invention relates to the value enhancement of byproducts of the direct synthesis (or Müller-Rochow synthesis) permitting the, production of methylchlorosilanes (MCS), which are base monomers for the manufacture of silicones by hydrolysis of Si—Cl bonds and creation, by polycondensation, of polysiloxanes containing siloxyl units "D" (—Me$_2$SiO$_{2/2}$—), "M" (—Me$_3$SiO—), "T" (—MeSiO$_{3/2}$—), "Q" (—SiO$_{4/2}$—). The direct synthesis takes place by reaction between metallic silicon and methyl chloride at a temperature of between 250 and 300° C. in the presence of a catalyst based on copper, zinc or tin. This synthesis leads to a mixture in which dimethylchlorosilane Me$_2$SiCl$_2$ is predominant (approximately 90%), but also to heavier products consisting primarily of disilanes (approximately 8%) of formula Me$_p$Cl$_{3-p}$—Si—Si—Cl$_{3-q}$Me$_q$ (p, q=1 or 2). Other, so-called "light" MCS are also formed at the outcome of this direct synthesis. These light MCS are produced in allow proportion. They comprise in particular MeSiCl$_3$ (7–18%), MeSiCl$_2$ (0.5%) and, in even smaller quantities, Me$_2$HSiCl, MeHSiCl$_2$, Me$_4$Si, HSiCl$_3$, and isopentane. The light MCS are present in the stream emerging from the head of one or more distillation columns. This distillation operation makes it possible to separate the various products of the direct synthesis.

Among the light MCS, MeSiCl$_2$ constitutes the building block for the formation of polysiloxane chains containing units D (—Me$_2$SiO—); Me$_3$SiCl serves as a chain-end blocker; MeSiCl$_3$ permits the crosslinking of the polymer; and the compounds MeHSiCl$_2$ and Me$_2$HSiCl enable the functionalization of the polymer through the use of the Si—H bond. Me$_2$HSiCl, which does not possess an Si—Cl bond, permits selective chain-end functionalization, which is particularly desired. Consequently, the relative value of the MCS in relation to Me$_2$HSiCl$_2$ (reference=1) is as follows:

Me$_2$HSiCl (10–100)>Me$_3$SiCl (2–3)>MeHSiCl$_2$ (0.5–1.5)) >MeSiCl$_3$ (0.1–0.2).

Industrially, the production of MeSiCl$_3$ far outstrips demand. The desire of those involved in industry would therefore be to enhance the value of MeSiCl$_3$. Since the hydromethylchlorosilanes Me$_2$HSiCl and MeHSiCl$_2$ are greatly desired, it is possible to envisage producing them from the methylchlorosilanes Me$_2$SiCl$_2$ and MeSiCl$_3$, respectively, which are widely available and inexpensive.

Accordingly, a number of processes have been proposed for hydrogenolyzing Si—Cl bonds present in ahs by molecular hydrogen, in accordance with the following reactions:

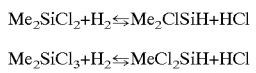

These reactions are catalyzed by at least one metallic compound.

Among the known processes of hydrogenating alkylhalosilanes, especially methylchlorosilanes, mention may be made of that described in the U.S. Pat. No. 5,329,038, wherein dimethyldichlorbsilane is hydrogenated using hydrogen gas in the presence of aluminum and a catalyst selected from the group consisting of copper, tin, zinc and derivatives of these metals.

The European patent application No. 717 900 describes the vapor-phase catalytic hydrogenation of alkylhalo (chloro)silanes to produce alkylhydrohalo(chloro)silanes in the presence of a metallic catalyst selected from the group consisting of palladium, platinum, ruthenium, optionally supported on active carbon and/or on aluminum oxide and/or on titanium oxide and/or on silicone oxide. More specifically, this European application describes the conversion of Me$_2$SiCl$_2$ into Me$_2$HSiCl, MeHSiCl$_2$ and Me$_3$SiCl. The catalysts employed in the examples are, respectively, palladium on active carbon, platinum on active carbon, and ruthenium on alumina. The gaseous hydrogen is mixed into the Me$_2$SiCl$_2$, which is also in gaseous form. The reaction temperatures are 340 and 400° C. under pressures of 2, 6 and 10 bar. It should be noted that, in order to obtain a selectivity for MeHSiCl$_2$ of the order of 50%, it is necessary, according to this process, to employ pressures of 6 and 10 bar, which are relatively difficult to manage at the industrial level.

The European patent application No. 714 901 possesses the same content as the application EP No. 714 900 studied above, except that in this case the hydrogenation catalyst employed is hexachloroplatinic acid.

Within such a state of the art, one of the essential objectives of the present invention is to provide a process for preparing alkylhydrohalosilanes ahhs, in particular monosilanes of the methylhydrochlorosilane kind, by catalytic hydrogenation of alkylhalosilanes (ahs) of the methylchlorosilane type in the presence of a metallic catalyst, the purpose of such a process being to permit the obtention of high selectivities for alkylhydrohalosilanes (especially for methylhydrochlorosilanes) without, moreover, it being necessary to utilize conditions which are drastic and poorly suited to use in industry (high pressure).

Another essential objective of the present invention is to provide a process for catalytic hydrogenation in vapor phase of alkylchlorosilanes, especially methylchlorosilanes, to give alkylhydrohalosilanes, especially methylhydrochlorosilanes, which is simple to carry out and cost effective.

Another essential objective of the invention is to provide a process for enhancing the value of MeSiCl$_3$ by catalytic hydrogenation in vapor phase of this byproduct of the direct synthesis, for the purpose of obtaining MeHSiCl$_2$ which may be usefully exploited in the production of graftable siloxyl units D or else converted into MeHSiCl by chlorine redistribution starting from Me$_3$SiCl (FR No. 96 07 559 and 97 16 047).

Another essential objective of the present invention is to provide a process for preparing alkylhydrohalosilanes (e.g., methylhydrochlorosilanes) by hydrogenating an alkylhalosilane (e.g., methylchlorosilane) using hydrogen gas in the presence of a metallic catalyst featuring particularly high performance and selectivity for MeH and further featuring a low cost price and obtainability on the industrial scale in a homogeneous form.

Another essential object of the invention is to provide a process for preparing ahhs by catalytic hydrogenation of ahs in the presence of a metal catalyst, the purpose of said process being to overcome the disadvantages of the prior art processes.

Given these objectives, among others, the inventors had the merit to select, after long and laborious research and experimentation, a specific ruthenium/tin catalyst which permits all of the abovementioned objectives to be attained, especially as regards selectivity for alkylhydrohalosilanes (MeHSiCl$_2$).

The present invention accordingly provides a process for preparing alkylhydrohalosilanes (ahhs) of formula (I):

$$R_{4-m-n} \text{SiH}_m X_n \quad (I)$$

in which
R represents independently a $C_1$–$C_6$ alkyl, preferably linear or branched, and more preferably still a methyl,
X represents independently a halogen, preferably chlorine,
m, n=1 or 2 and m+n$\leq$3
by catalytic hydrogenation of alkylhalosilanes (ahs) of formula (II):

$$—R_{(4-f)} \text{Si}_f \quad (II)$$

where f=1, 2 or 3 in accordance with the reaction:

$$R_{(4-p)} \text{Si } X_p + H_2 \rightarrow R_{4-m-n} \text{SiH}_m X_n + H_{m'} X_{n'}$$

where n'+n=p and m'=0 or 1
in the presence of a metallic catalyst, characterized in that the catalyst comprises a bimetallic ruthenium/tin catalytic agent.

One of the fundaments of the present invention is therefore the selection of a particular metallic catalyst which makes it possible to achieve high selectivities for MeHSiCl$_2$ when the hydrogenation starting material consists of MeSiCl$_3$.

The catalytic agents selected in the process of the invention may advantageously be defined through the method of obtaining it. Accordingly, preferentially, said catalytic agent is obtained from the reduction of a ruthenium complex having an electrovalence of –4 and a coordination number of 6, the ligands being either a halogen atom or an anion of a tin halide.

More preferably still, the complex corresponds to the following formula (A)

$$[\text{Ru}(\text{SnX}_3)_{6-n} X_n]^{4-} \quad (A);$$

in said formula (A), X represents a halogen atom, preferably an atom of chlorine or bromine, and n is a number from 0 to 2, preferably 1.

In one advantageous embodiment of the process of the invention, the following complexes are employed as catalytic agents:

$$—[\text{Ru}(\text{SnCl}_3)_6]^{4-} \quad (A_1)$$

$$—[\text{Ru}(\text{SnCl}_3)_5 \text{Cl}]^{4-} \quad (A_2)$$

$$—[\text{Ru}(\text{SnCl}_3)_4 \text{Cl}_2]^{4-} \quad (A_3)$$

The ruthenium and tin halogen complex, selected in accordance with the invention and corresponding preferably to the formulae (A$_1$) to (A$_3$), has the not inconsiderable advantage of being of high quality when obtained as indicated above.

More specifically and more advantageously, this complex may be produced by reacting a ruthenium halide and a tin halide in the presence of an acid.

In practice, and without limitation, the ruthenium halide is a ruthenium(III) halide, in anhydrous or hydrated form, preferably a ruthenium(III) chloride, and the tin(II) halide, in anhydrous or hydrated form, is preferably tin(II) chloride.

For further details regarding the ruthenium/tin catalytic agent used in the process of the invention, reference may be made to the patent application FR 9 513 185, which substantially describes this catalytic agent in terms of obtention and structure.

According to one preferred embodiment of the catalytic hydrogenation process of the invention, a catalyst is used which comprises at least one solid support impregnated with at least one catalytic agent as defined above by the method by which it is obtained. Still in accordance with this preferred embodiment, it is advantageous for the support to be in the form of powder, beads, granules or extrudates, inter alia.

In practice, the support is selected from metal oxides, preferably the oxides of aluminum, of silicon or of zirconium, active carbons, and resins.

With regard to optimizing the process of the invention, it is preferable for the catalyst to have a ruthenium concentration [Ru] defined as follows in % by weight on a dry basis:
0.1$\leq$[Ru]$\leq$20,
preferably
0.4$\leq$[Ru]$\leq$10,
and more preferably still
1$\leq$[Ru]$\leq$8.

In the context of selecting the catalyst according to the invention, it is advantageous for the Sn/Ru molar ratio of the catalyst to be defined as follows:
0.1$\leq$Sn/Ru$\leq$30,
preferably
0.4$\leq$Sn/Ru$\leq$10,
and more preferably still
1$\leq$Sn/Ru$\leq$8.

Regarding the other parameters of employment of the process of the invention, it is useful to specify that the hydrogenation of ahs (II) to ahhs(I) is preferably carried out at a reaction temperature $\theta r$ defined as follows in ° C.:
200$\leq$$\theta r$$\leq$600,
preferably
400$\leq$$\theta r$$\leq$500.

As regards the reaction pressure preferred in accordance with the invention, it is possible to specify that it is in practice less than 2 bar and, preferably, corresponds substantially to atmospheric pressure.

Insofar as the stoichiometry of the reaction at the heart of the process in accordance with the invention is concerned, it is preferred that it is such that the H$_2$/ahs (II) ratio is defined as follows in equivalents:
1$\leq$H$_2$/(II)$\leq$100,
preferably
10$\leq$H$_2$/(II)$\leq$20.

According to one preferred embodiment of the invention, the vapor phase hydrogenation of ahs (II) is carried out by heterogeneous catalysis.

It is obvious that, within an industrial system, it is preferable for the process of the invention to be employed continuously, taking measures to ensure that the gas flow rate of the reactants employed, for example MeSiCl$_3$ and hydrogen gas, are such that the contact time Tc of said reactants H$_2$ and ahs (II) with the catalyst is:

between 0.1 and 100 s and more preferably still between 0.1 and 10 s.

Advantageously, the hydrogenation of (II) to (I) is carried out at atmospheric pressure.

In one advantageous embodiment of the invention, the reactive hydrogen gas employed is mixed with at least one gaseous diluent selected preferably from inert gases, more particular preference being given to nitrogen.

In practice, the diluent gas or gases may represent, for example, from 40 to 60% by volume of the hydrogen gas reagent, preferably approximately 50%.

Regarding the substrate ahs (II) to be hydrogenated, it preferably comprises $MeSiCl_3$, which is converted into $MeHSiCl_2+HCl$.

Owing to the selectivity for MeH which it enables to be attained, the process of the invention offers an advantageous route for enhancing the value of low added value byproducts of the direct synthesis, such as $MeSiCl_3$.

Moreover, this does not exclude the process of the invention possibly being applied to $Me_2SiCl_2$, it being understood that in such a case it is evidently not the value enhancement which is intended.

The selection of the appropriate device for implementing the process of the invention is a procedure which is entirely within the scope of the skilled worker.

In any case, the examples which follow will enable better understanding of the invention and perception of all of its advantages and embodiments. Furthermore, these examples provide an illustration of the type of device which may be suitable for implementing the process.

EXAMPLE 1

Vapor Phase Catalytic Hydrogenation of $CH_3SiCl_3$ (ahs (II)=Me) to $CH_3SiHCl_2$ (ahhs (I)=MeH)

1.1 Preparation of the Ru/Sn catalyst supported on a silica powder 5.04 g of $RuCl_3 \cdot x H_2O$ containing 42% by weight of ruthenium and 27.7 g of $SnCl_2 \cdot 2H_2O$ and 180 ml of a 3N aqueous solution of hydrochloric acid are introduced into a three-necked flask.

The mixture is heated with stirring at 90° C. for 1 hour. This solution is subsequently cooled to 20° C.

Then 40 g of Degussa 0×50 silica (specific surface area= 50 m²/g and average primary particle size (=40 nm) and 400 ml of water are added.

The precipitate is filtered off and washed with water.

The filter cake is subsequently ground and extruded.

The extrudates are subsequently dried in air to constant weight.

The catalyst is subsequently treated with hydrogen at 450° C. under a stream of hydrogen for 4 hours.

A catalyst is obtained which is formed by a powder $[Ru(SnCl_3)_5Cl]^{5-}$ on $SiO_2$ in which [Ru]=5% by dry of weight relative to the total mass of the catalyst, and Sn/Ru= 6.

By varying the proportions, [Ru] and Sn/Ru are modified at will.

1.2 Apparatus and Methodology

A glass reactor is used consisting of a column including internal means of heating to θr, consisting of a EUROTHERM-regulated electric oven. The head of this column has an Me feed line and an $H_2$ feed line.

The bottom of this column is shaped to form a discharge line for the mixture of gases produced. The bottom half of the column comprises a fixed catalyst bed arranged in the aperture of the column. This bed comprises three superposed layers of quartz (5 ml), of catalyst $[Ru(SnCl_3)_5Cl]^{5-}$ on $SiO_2$, obtained in 1.1 above (5 ml), and of quartz (5 ml) respectively.

A thermometer is provided for measuring θr inside the catalyst bed.

The peripherals associated at the entry of the column are sources of $H_2$ and of Me and means of injecting $H_2$ and Me (II) at controlled flow rates (syringe/syringe pusher), (flask of $H_2$ under pressure). The peripherals associated with the exit of the valve and the column are means of cooling the gaseous reaction mixture produced (ice and dry-ice trap) to condense it to a liquid.

The reaction parameters are:

θr

[Ru]

Sn/Ru

Me (II) flow rate, for example 0.5 ml/hour $H_2$ flow rate, for example 600 ml/hour volume (V) of catalyst=5 ml for all the tests contact time $T_c$ of the Me and $H_2$ reactant mixture with the catalyst depends on the $H_2$ and Me (II) flow rates and is determined as indicated below:

$V_1$=volume of Me (II) at θr (ml/s)

$V_2$=volume of $H_2$ at θr (ml/s)

V=volume of catalyst (ml)

$$T_c = \frac{V}{V_1 + V_2} (s)$$

EXAMPLE 2

Comparative Tests 1C, 2C and 3C and Tests 4 to 12

The chromatographic analyses are carried out by gas chromatography.

Table 1 below gives the reaction conditions and the results obtained.

TABLE 1

| Test No. | Catalyst Nature | [Ru] % | Sn/Ru | θr ° C. | $H_2$ flow rate ml/h | Me flow rate ml/h | $T_c$ s | $\frac{H_2}{Me}$ | Productanalysis(mmol) MeH (I) | $SiCl_4$ | $Me_2$ | Total | YMeH % (I) | YSiCl % | YMe % |
|---|---|---|---|---|---|---|---|---|---|---|---|---|---|---|---|
| 1 c | Pd 5%/C | | | 450 | 6000 | 0.4 | 1.12 | 73 | 16.522 | 61.706 | 28.915 | 109.142 | 15.14 | 58.37 | 26.49 |
| 2 c | Ru only | 100 | 0 | 450 | 6000 | 0.5 | 1.12 | 77 | 0.426 | 0.000 | 25.279 | 25.705 | 1.60 | 0.00 | 93.84 |
| 3 c | Ru only | 100 | 0 | 450 | 6000 | 0.5 | 1.12 | 76 | 0.391 | 0.000 | 12.240 | 12.632 | 3.10 | 0.00 | 96.90 |
| 4 | Ru/Sn | 5 | 6 | 450 | 6000 | 0.4 | 1.12 | 76 | 15.217 | 4.559 | 15.736 | 35.513 | 42.85 | 12.84 | 44.31 |

TABLE 1-continued

| Test No. | Catalyst Nature | [Ru] % | Sn/Ru | $\theta_r$ °C. | $H_2$ flow rate ml/h | Me flow rate ml/h | $T_c$ s | $\frac{H_2}{Me}$ | Product analysis (mmol) MeH (I) | $SiCl_4$ | $Me_2$ | Total | YMeH % (I) | YSiCl % | YMe % |
|---|---|---|---|---|---|---|---|---|---|---|---|---|---|---|---|
| 5 | Ru/Sn | 5 | 6 | 450 | 6000 | 0.4 | 1.12 | 74 | 15.339 | 5.341 | 14.589 | 35.269 | 43.49 | 15.14 | 41.36 |
| 6 | Ru/Sn | 5 | 6 | 450 | 6000 | 0.4 | 1.12 | ?? | 19.904 | 4.518 | 15.101 | 39.523 | 50.36 | 11.43 | 38.21 |
| 7 | Ru/Sn | 5 | 6 | 450 | 6000 | 0.4 | 1.12 | 80 | 15.539 | 4.247 | 14.116 | 39.902 | 45.83 | 12.51 | 41.64 |
| 8 | Ru/Sn | 5 | 6 | 450 | 6000 | 0.4 | 1.12 | 79 | 18.539 | 3.935 | 13.969 | 36.443 | 50.87 | 10.80 | 38.33 |
| 9 | Ru/Sn | 5 | 6 | 450 | 6000 | 0.4 | 1.12 | 79 | 20.287 | 4.429 | 14.039 | 38.755 | 52.35 | 11.43 | 36.22 |
| 10* | Ru/Sn | 5 | 6 | 450 | 3000 of $H_2$ and 3000 of $N_2$ | 0.4 | 1.12 | 77 | 11.035 | 4.165 | 13.558 | 28.758 | 38.37 | 14.48 | 47.15 |
| 11 | Ru/Sn | 5 | 6 | 450 | 6000 | 0.4 | 1.79 | 81 | 15.313 | 3.494 | 12.876 | 31.683 | 48.33 | 11.03 | 40.64 |
| 12 | Ru/Sn | 5 | 6 | 450 | 6000 | 0.4 | 1.79 | 79 | 16.487 | 6.535 | 15.814 | 38.836 | 42.45 | 16.83 | 40.72 |

*The gas flow consists of 3000 ml of hydrogen and 3000 ml of nitrogen.

What is claimed is:

1. A process for preparing alkylhydrohalosilanes (ahhs) of formula (I)

$$R_{4-m-n} SiH_m X_n \quad (I)$$

in which
R represents independently a $C_1$–$C_6$ alkyl,
X represents independently a halogen,
m, n are 1 or 2 and m+n≦3
comprising hydrogenating catalytically alkylhalosilanes (ahs) of formula (II):

$$R_{(4-f)} Si X_f \quad (II)$$

where f is 1, 2 or 3
in accordance with the reaction:

$$R_{(4-p)} Si X_p + H_2 \rightarrow R_{4-m-n} SiH_m X_n + H_{m'} X_{n'}$$

where n'+n=p and m' is 0 or 1
in the presence of a metallic catalyst,
wherein the metallic catalyst comprises a bimetallic ruthenium/tin catalytic agent.

2. The process of claim 1, further comprising obtaining the catalytic agent by reducing a ruthenium complex having an electrovalence of −4 and a coordination number of 6, the ligands being either a halogen atom or an anion of a tin halide.

3. The process of claim 2, wherein the complex corresponds to the following formula (A):

$$[Ru(SnX_3)_{6-n}X_n]^{4-} \quad (A);$$

and wherein in said formula (A), X represents a halogen atom, and n is a number from 0 to 2.

4. The process of claim 2, wherein the complex of formula (A) is:

—[Ru(SnCl$_3$)$_6$]$^{4-}$ (A$_1$),

—[Ru(SnCl$_3$)$_5$Cl]$^{4-}$ (A$_2$), or

—[Ru(SnCl$_3$)$_4$Cl$_2$]$^{4-}$ (A$_3$).

5. The process of claim 2, further comprising preparing the complex by reacting a ruthenium halide and a tin halide in the presence of an acid.

6. The process of claim 5, wherein the ruthenium halide is a ruthenium (III) halide, in anhydrous or hydrated form, and the tin (II) halide in anhydrous or hydrated form.

7. The process of claim 1, wherein the catalyst comprises at least one solid support impregnated with at least one catalytic agent obtained by reducing a ruthenium complex having an electrovalence of −4 and a coordination number of 6, the ligands being either a halogen atom or an anion of a tin halide.

8. The process of claim 7, wherein the support is in the form of powder, beads, granules, or extrudates.

9. The process of claim 7, wherein the support is a metal oxide, an active carbon, and a resin.

10. The process of claim 1, wherein the catalyst has a ruthenium concentration [Ru] of:
0.1%≦[Ru]≦20% by dry weight.

11. The process of claim 1, wherein the Sn/Ru molar ratio of the catalyst is:
0.1≦Sn/Ru≦30.

12. The process of claim 1, wherein the step of hydrogenating ahs (II) to ahhs (I) is carried out at a reaction temperature (θr) of greater than or equal to 200° C. to less than or equal to 600° C.

13. The process of claim 1, wherein the stoichiometry of the reaction has a $H_2$/ahs (II) ratio of:
1≦$H_2$/(II)≦100.

14. The process of claim 1, wherein the vapor phase hydrogenation of ahs (II) is carried out by heterogeneous catalysis.

15. The process of claim 1, wherein the contact time $T_c$ of the reactants $H_2$ and ahs (II) with the catalyst is between 0.1 and 100 seconds.

16. The process of claim 1, wherein the step of hydrogenating formula (II) to formula (I) is carried out at atmospheric pressure.

17. The process of claim 1, further comprising mixing the $H_2$ gas with at least one gaseous diluent.

18. The process of claim 1, wherein the $C_1$–$C_6$ alkyl is a linear or branched alkyl.

19. The process of claim 1, wherein the $C_1$–$C_6$ alkyl is a methyl.

20. The process of claim 1, wherein X is chlorine.

21. The process of claim 3, wherein X of formula (A) is chlorine or bromine.

22. The process of claim 3, wherein n of formula (A) is 1.

23. The process of claim 6, wherein the ruthenium (II) halide is ruthenium (III) chloride.

24. The process of claim 6, wherein the tin (II) halide is tin (II) chloride.

25. The process of claim 9, wherein the metal oxide is an oxide of aluminum, silicon, or zirconium.

26. The process of claim 10, wherein the ruthenium concentration [Ru] is greater than or equal to 0.4 to less than or equal to 10% weight on a dry basis.

27. The process of claim 10, wherein the catalyst has a ruthenium concentration [Ru] of greater than or equal to 1 to about less than or equal to 8% by weight on a dry basis.

28. The process of claim 11, wherein the Sn/Ru molar ratio of the catalyst is greater than or equal to 0.4 to less than or equal to 10.

29. The process of claim 11, wherein the Sn/Ru molar ratio of the catalyst is greater than or equal to 1 to less than or equal to 8.

30. The process of claim 12, wherein the reaction temperature ($\theta r$) is greater than or equal to 400° C. to less than or equal to 500° C.

31. The process of claim 13, wherein the stoichiometry of the reaction has a $H_2$/ahs (II) ratio of $10 \leq H_2/(II) \leq 20$.

32. The process of claim 15, wherein the contact time is between 0.1 and 10 seconds.

33. The process of claim 17, wherein the gaseous diluent is an inert gas.

34. The process of claim 33, wherein the inert gas is nitrogen.

* * * * *